(12) United States Patent
Constantinides et al.

(10) Patent No.: US 8,865,144 B2
(45) Date of Patent: *Oct. 21, 2014

(54) PERSONAL CARE COMPOSITIONS COMPRISING RESPONSIVE PARTICLES

(75) Inventors: Ioannis Constantine Constantinides, Wyoming, OH (US); Robert J. Willicut, Liberty Township, OH (US); Ellen Schmidt Baker, Cincinnati, OH (US); Howard David Hutton, III, Cincinnati, OH (US); Timothy James Felts, Hamilton, OH (US); Lee Arnold Schechtman, Fairfield, OH (US); Sergiy Minko, Potsdam, NY (US); Mikhail Motornov, Potsdam, NY (US)

(73) Assignee: The Procter & Gamble Company, Cincinnati, OH (US)

(*) Notice: Subject to any disclaimer, the term of this patent is extended or adjusted under 35 U.S.C. 154(b) by 918 days.

This patent is subject to a terminal disclaimer.

(21) Appl. No.: 11/705,888

(22) Filed: Feb. 14, 2007

(65) Prior Publication Data

US 2007/0196299 A1    Aug. 23, 2007

Related U.S. Application Data

(60) Provisional application No. 60/773,046, filed on Feb. 14, 2006, provisional application No. 60/773,260, filed on Feb. 14, 2006.

(51) Int. Cl.

| | |
|---|---|
| *A61K 8/00* | (2006.01) |
| *A61K 8/81* | (2006.01) |
| *A61K 8/18* | (2006.01) |
| *A61K 8/72* | (2006.01) |
| *A61K 8/19* | (2006.01) |
| *A61K 8/49* | (2006.01) |
| *A61K 8/11* | (2006.01) |
| *A61Q 19/00* | (2006.01) |
| *A61Q 1/02* | (2006.01) |
| *A61K 8/29* | (2006.01) |

(52) U.S. Cl.
CPC ... *A61Q 1/02* (2013.01); *A61K 8/11* (2013.01); *A61K 2800/412* (2013.01); *A61Q 19/00* (2013.01); *A61K 8/29* (2013.01)
USPC .............. 424/70.11; 424/63; 424/64; 424/73; 424/61; 424/70.1

(58) Field of Classification Search
None
See application file for complete search history.

(56) References Cited

U.S. PATENT DOCUMENTS

| | | | |
|---|---|---|---|
| 5,618,524 A * | 4/1997 | Bolich et al. | ............... 424/70.12 |
| 5,997,887 A | 12/1999 | Ha et al. | |
| 6,268,048 B1 | 7/2001 | Topolkaraev et al. | |
| 6,451,895 B1 | 9/2002 | Topolkaraev et al. | |
| 6,492,326 B1 | 12/2002 | Robinson et al. | |
| 6,696,050 B2 * | 2/2004 | Barbuzzi et al. | ............ 424/70.11 |
| 6,793,913 B2 * | 9/2004 | Tournilhac et al. | ............ 424/401 |
| 2002/0176833 A1 * | 11/2002 | Nagatani et al. | ................ 424/63 |
| 2003/0012757 A1 * | 1/2003 | Barbuzzi et al. | ............. 424/70.1 |
| 2005/0163714 A1 | 7/2005 | Sukhishvili et al. | |
| 2008/0175906 A1 * | 7/2008 | Ahmed et al. | ................. 424/464 |

OTHER PUBLICATIONS

International Search Report, PCT/US2007/003981, dated Jul. 25, 2007 (5 pages).
C.M. Pande and J. Jachowicz, J. Soc. Cosmet. Chem. 44, 109-122, 1993.

* cited by examiner

*Primary Examiner* — Scott Long
*Assistant Examiner* — Sarah Alawadi
(74) *Attorney, Agent, or Firm* — Angela K. Haughey

(57) ABSTRACT

Personal care compositions comprising responsive particles. In one aspect, the responsive particle comprises: (1) a particle core having an interfacial surface, (2) a first polymer having a first property, and (3) a second polymer having a contrasting property. The first polymer and the second polymer are attached at different locations to the interfacial surface of the particle core. In another aspect, the responsive particle comprises: (1) a particle core having an interfacial surface, (2) at least one block co-polymer comprising a first block and a second block, wherein said first block has a first property and said second block has a second property, and (3) optionally, at least one other polymer having a third property. The block co-polymer and the optional other polymer (if present) are attached to the interfacial surface of the particle core, and at least one of the properties contrasts. The personal care compositions also comprise a dermatologically acceptable carrier. Also disclosed are methods of making responsive particles.

6 Claims, No Drawings

PERSONAL CARE COMPOSITIONS COMPRISING RESPONSIVE PARTICLES

CROSS-REFERENCE TO RELATED APPLICATIONS

This application claims the benefit of priority to U.S. Provisional Application Ser. No. 60/773,046 (P&G Case 10305P) and 60/773,260 (P&G Case 10306P), filed Feb. 14, 2006, both of which are herein incorporated by reference.

TECHNICAL FIELD

The present invention relates to personal care compositions comprising responsive particles and methods for making such particles. Such compositions are useful for regulating the condition of mammalian keratinous tissue (e.g., skin, hair, and/or nails).

BACKGROUND

Skin, hair, and nails are subject to insults by many extrinsic and intrinsic factors. Extrinsic factors include ultraviolet radiation (e.g., from sun exposure), environmental pollution, wind, heat, humidity extremes, harsh surfactants, abrasives, and the like. Intrinsic factors include chronological aging and other biochemical changes from within the skin, hair, or nails. Whether extrinsic or intrinsic, these factors result in visible signs of skin, hair, and nail aging and environmental damage (e.g., such as sunlight damage, smoke damage, and damage from pollutants such as nitrogen oxides, sulfur oxides, ozone, and metals such as lead).

In addition to the visible signs that result from damage and/or aging of keratinous tissue (e.g., hair, skin, and nails), changes also occur in the keratinous tissues' chemical and/or physical properties. For instance, healthy undamaged human hair is hydrophobic. However, when the hair becomes oxidized and/or damaged, the hair becomes hydrophilic. Furthermore, some regions of hair may be more damaged than others, leading to hydrophilic hair in some areas but hydrophobic in others. This heterogeneity of properties makes it difficult to deliver a consistent, uniform benefit to the entire head of hair (e.g., conditioning, coloring, etc.), since the varying hair properties affect the performance of the hair care composition that is applied.

Similar problems exist with the application of skin care products to skin. Skin undergoes a change in surface energy when it is damaged and/or aged. As with hair, the properties of the skin thus vary across different regions of the skin's surface. This heterogeneity makes it difficult to deliver a consistent, uniform benefit to the entire skin surface to be treated, since the varying skin properties affect the performance of the skin care composition that is applied.

In addition, certain materials in personal care formulations can undesirably accumulate on keratinous substrates (e.g. hair and/or skin) to create aesthetic or functional negatives. This can result from incompatibility of the materials with compositions made to cleanse and/or remove them. For example, silicone polymer-based conditioner products can excessively accumulate on the hair surface with repeated application, resulting in a greasy look and/or feel. Ideally, the conditioning agent would be removed with each shampooing and a new layer deposited.

Furthermore, many desired benefit agents are not compatible (e.g., soluble, miscible, dispersible) with the preferred delivery vehicle. For example, it can be difficult to formulate, stabilize, and/or deliver a hydrophobic benefit agent in a predominantly water-based (hydrophilic) composition.

Accordingly, there is a need for personal care compositions that provide a uniform benefit to keratinous tissue regardless of the keratinous tissue's non-uniformity of chemical and/or physical properties. Furthermore, there is a need for personal care compositions that do not undesirably accumulate on keratinous tissue despite removal efforts. In addition, there is a need for personal care compositions that can deliver benefit agents that are considered incompatible with the preferred delivery vehicle.

SUMMARY

The present invention provides personal care compositions that can adapt to provide uniform benefits to keratinous tissue regardless of the keratinous tissue's non-uniformity of chemical and/or physical properties. Furthermore, the present invention provides personal care compositions that do not undesirably accumulate on keratinous tissue despite removal efforts. In addition, the personal care compositions of the present invention can deliver benefit agents that are considered incompatible with the preferred delivery vehicle.

These personal care compositions comprise responsive particles. In one embodiment, the responsive particle comprises: (1) a particle core having an interfacial surface, (2) a first polymer having a first property, and (3) a second polymer having a contrasting property. The first polymer and the second polymer are attached at different locations to the interfacial surface of the particle core. The personal care compositions also comprise a dermatologically acceptable carrier. In some embodiments, the responsive particle comprises more than two polymers and/or properties.

In yet another embodiment, the responsive particle comprises: (1) a particle core having an interfacial surface, (2) at least one block co-polymer comprising a first block and a second block, wherein said first block has a first property and said second block has a second property, and (3) optionally, at least one other polymer having a third property. The block co-polymer and the optional other polymer (if present) are attached to the interfacial surface of the particle core, and at least one of the properties contrasts. In some embodiments, the block co-polymer comprises more than two blocks and/or polymers and/or properties.

In another aspect, the present invention provides methods for making responsive particles for use in personal care compositions. The method comprises: (1) providing a dermatologically acceptable particle having an interfacial surface, (2) attaching a first dermatologically acceptable polymer having a first property to said interfacial surface; and (3) attaching a second dermatologically polymer having a contrasting property to said interfacial surface.

In another embodiment, the method for making a responsive particle for use in personal care compositions comprises: (1) providing a dermatologically acceptable particle having an interfacial surface, (2) attaching at least one dermatologically acceptable block co-polymer comprising a first block and a second block to said interfacial surface, wherein said first block has a first property and said second block has a second property; and (3) optionally attaching at least one other dermatologically acceptable polymer having a third property to said interfacial surface, wherein at least one of the properties contrasts.

DETAILED DESCRIPTION

All percentages and ratios used herein are by weight of the total composition and all measurements made are at 25° C., unless otherwise designated.

The term "keratinous tissue," as used herein, refers to keratin-containing layers disposed as the outermost protective covering of mammals (e.g., humans, dogs, cats, etc.) which includes, but is not limited to the outer layers of skin mucosa, lips, hair, toenails, fingernails, cuticles, hooves, etc.

The terms "topical application", "topically", and "topical", as used herein, mean to apply (e.g., spread, spray) the compositions of the present invention onto the surface of the keratinous tissue.

The term "dermatologically acceptable," as used herein, means that the compositions or components thereof so described are suitable for use in contact with mammalian keratinous tissue without undue toxicity, incompatibility, instability, allergic response, and the like.

The personal care compositions of the present invention can be useful for treating keratinous tissue (e.g., hair, skin, or nails) condition. As use herein, "treating" or "treatment" or "treat" includes regulating and/or immediately improving keratinous tissue cosmetic appearance and/or feel. As used herein, "regulating" or "regulation" means maintaining or improving the health and/or cosmetic appearance, and includes both prophylactically regulating and/or therapeutically regulating. Regulation of keratinous tissue condition, namely mammalian and in particular human skin, hair, sebaceous gland or nail condition, is often required due to conditions which may be induced or caused by factors internal and/or external to the body. Examples include environmental damage, radiation exposure (including ultraviolet radiation), chronological aging, menopausal status (e.g., post-menopausal changes in skin, hair, sebaceous glands, or nails), stress, diseases, disorders, etc. For instance, "regulating skin, hair, sebaceous glands, or nail condition" includes prophylactically regulating and/or therapeutically regulating skin, hair, sebaceous glands, or nail condition, and may involve one or more of the following benefits: thickening of skin, hair, or nails (e.g., building the epidermis and/or dermis and/or subdermal [e.g., subcutaneous fat or muscle] layers of the skin, and where applicable the keratinous layers of the nail and hair shaft) to reduce skin, hair, or nail atrophy, increasing the convolution of the dermal-epidermal border (also known as the rete ridges), preventing loss of skin or hair elasticity (loss, damage and/or inactivation of functional skin elastin) such as elastosis, sagging, loss of skin or hair recoil from deformation; melanin or non-melanin change in coloration to the skin, hair, or nails such as under eye circles, blotching (e.g., uneven red coloration due to, e.g., rosacea) (hereinafter referred to as "red blotchiness"), sallowness (pale color), discoloration caused by telangiectasia or spider vessels, and graying hair, and reducing pore size.

Furthermore, the personal care compositions of the present invention can be useful for cleansing, conditioning, or protecting keratinous tissue. For instance, such compositions can be used for removing sebum, removing residues from hair care products, delivering conditioning agents to hair for improved feel (e.g., softness) and/or shine, improving combability of hair, modifying hair volume, protecting from humidity, protecting from the sun, protecting from the environment, protecting hair color (e.g., preventing fade), delivering hair color, delivering antistatic properties, improving wet-handling, preventing damage, improving body, decreasing greasiness, and controlling frizz.

As used herein, "personal care composition" includes any product applied topically to keratinous tissue (e.g., skin, hair, nails).

The compositions of the present invention can also be useful for immediately improving keratinous tissue (e.g., skin, hair, or nail) cosmetic appearance and/or feel. For example, topical compositions of the present invention can be useful for regulating the cosmetic appearance of skin, hair, or nail condition by providing an immediate visual improvement in skin, hair, or nail appearance following application of the composition to the skin, hair, or nails. Generally speaking, topical compositions of the present invention which further contain particulate materials (e.g., pigments) can be most useful for providing immediate visual improvement.

"Signs of keratinous tissue aging" include, but are not limited to, all outward visibly and tactilely perceptible manifestations as well as any other macro or micro effects due to keratinous tissue aging. Such signs may be induced or caused by intrinsic factors or extrinsic factors, e.g., chronological aging and/or environmental damage. These signs may result from processes which include, but are not limited to, the development of textural discontinuities such as wrinkles and coarse deep wrinkles, fine lines, skin lines, crevices, bumps, large pores (e.g., associated with adnexal structures such as sweat gland ducts, sebaceous glands, or hair follicles), or unevenness or roughness, loss of skin elasticity (loss and/or inactivation of functional skin elastin), sagging (including puffiness in the eye area and jowls), loss of skin firmness, loss of skin tightness, loss of skin recoil from deformation, discoloration (including undereye circles), blotching, sallowness, hyperpigmented skin regions such as age spots and freckles, keratoses, abnormal differentiation, hyperkeratinization, elastosis, collagen breakdown, and other histological changes in the stratum corneum, dermis, epidermis, the skin vascular system (e.g., telangiectasia or spider vessels), and underlying tissues (e.g., fat and/or muscle), especially those proximate to the skin.

The personal care compositions of the present invention can be in any suitable form. All forms of topical personal care compositions are contemplated and can include, for instance, creams, gels, lotions, emulsions, colloids, solutions, suspensions, ointments, milks, sprays, capsules, tablets, liquids, sticks, solids, powders, compacts, pencils, spray-on formulations, brush-on formulations, cloths, wipes, and the like.

Non-limiting examples of topical personal care compositions can include, without limitation, lipstick, mascara, rouge, foundation, blush, eyeliner, lipliner, lip gloss, facial powder, body powder, sunscreen, sun block, nail polish, mousse, spray, styling gel, nail conditioner, bath gel, shower gel, shampoo, conditioner, cream rinse, hair dye, hair coloring product, hair conditioner, lip balm, skin conditioner, cold cream, moisturizer, hair spray, soap, body scrub, exfoliant, astringent, depilatory, permanent waving solution, antidandruff formulation, antiperspirant composition, deodorant, shaving product, preshaving product, after shaving product, cleanser, skin gel, and rinse. Furthermore, the composition can be applied topically through the use of a patch or other delivery device. Delivery devices can include, but are not limited to, those that can be heated or cooled, as well as those that utilize iontophoresis or ultrasound.

Responsive Particle

Any suitable particle core can be used, depending upon the desired attributes of the particular personal care composition. For example, a particle core can be organic, inorganic, a single particle, or an agglomerate of particles.

In some instances, nanoparticles, either individually or as an agglomerate, can be preferred for use as the particle core in personal care compositions. As used herein, the term nanoparticle (either individually or as an aggregate) refers to a particle that is less than 500 nanometers in its longest dimension. In one embodiment, the nanoparticles are from 1 to 500 nanometers, in another embodiment from 150 to 250 nanometers, and in another embodiment the nanoparticles are from 50 to 100 nanometers.

The desired beauty benefit can guide the choice of the particle core to be used for any particular personal care composition. For example, if sun protection is desired, a light-scattering particle (or agglomeration of particles), such as zinc oxide and/or titanium dioxide, can be used as the particle core.

Other nonlimiting examples of materials that can be used to form the particle core include colored and uncolored pigments, interference pigments, inorganic powders, organic powders, composite powders, optical brightener particles, and combinations thereof. These particulates can, for instance, be platelet shaped, spherical, elongated or needle-shaped, or irregularly shaped, surface coated or uncoated, porous or non-porous, charged or uncharged. Specific materials can include, but are not limited to, bismuth oxychloride, sericite, mica, mica treated with barium sulfate or other materials, zeolite, kaolin, silica, boron nitride, lauroyl lysine, nylon, polyethylene, talc, styrene, polypropylene, polystyrene, ethylene/acrylic acid copolymer, aluminum oxide, silicone resin, barium sulfate, calcium carbonate, cellulose acetate, PTFE, polymethyl methacrylate, starch, modified starches such as aluminum starch octenyl succinate, silk, glass, and mixtures thereof. Organic powders/fillers can include, but are not limited, to polymeric particles chosen from the methylsilsesquioxane resin microspheres such as, for example, those sold by Toshiba silicone under the name Tospearl 145A, microspheres of polymethylmethacrylates such as those sold by Seppic under the name Micropearl M 100, the spherical particles of crosslinked polydimethylsiloxanes, especially such as those sold by Dow Corning Toray Silicone under the name Trefil E 506C or Trefil E 505C, sphericle particles of polyamide and more specifically Nylon 12, especially such as those sold by Atochem under the name Orgasol 2002D Nat C05, polystyrene microspheres such as for example those sold by Dyno Particles under the name Dynospheres, ethylene acrylate copolymer sold by Kobo under the name FloBead EA209, PTFE, polypropylene, aluminium starch ocetenylsuccinate such as those sold by National Starch under the name Dry Flo, microspheres of polyethylene such as those sold by Equistar under the name of Microthene FN510-00, silicone resin, polymethylsilsesquioxane silicone polymer, platelet shaped powder made from L-lauroyl lysine, and mixtures thereof.

Also useful herein are interference pigments. Interference pigments, for purposes of the present specification, are defined as thin platelike layered particles having two or more layers of controlled thickness with different refractive indices that yield a characteristic reflected color from the interference of typically two, but occasionally more, light reflections, from different layers of the platelike particle. The most common examples of interference pigments are micas layered with about 50-300 nm films of $TiO_2$, $Fe_2O_3$, silica, tin oxide, and/or Cr2O3. Such pigments are often pearlescent. Pearl pigments reflect, refract and transmit light because of the transparency of pigment particles and the large difference in the refractive index of mica platelets and, for example, the titanium dioxide coating. Useful intereference pigments are available commercially from a wide variety of suppliers, for example, Rona (Timiron™ and Dichrona™), Presperse (Flonac™), Englehard (Duochrome™), Kobo (SK-45-R and SK-45-G), BASF (Sicopearls) and Eckart (e.g. Prestige Silk Red). Especially preferred are interference pigments with smaller particle sizes, with an average diameter of individual particles less than about 75 microns in the longest direction, preferably with an average diameter less than about 50 microns.

Other pigments useful in the present invention can provide color primarily through selective absorption of specific wavelengths of visible light, and include inorganic pigments, organic pigments and combinations thereof. Examples of such useful inorganic pigments include iron oxides, ferric ammonium ferrocyanide, manganese violet, ultramarine blue, and Chrome oxide. Organic pigments can include natural colorants and synthetic monomeric and polymeric colorants. An example is phthalocyanine blue and green pigment. Also useful are lakes, primary FD&C or D&C lakes and blends thereof. Also useful are encapsulated soluble or insoluble dyes and other colorants. Inorganic white or uncolored pigments useful in the present invention, for example $TiO_2$, $ZnO$, or $ZrO_2$, are commercially available from a number of sources. One example of a suitable particulate material contains the material available from U.S. Cosmetics (TRONOX $TiO_2$ series, SAT-T CR837, a rutile $TiO_2$). Particularly preferred are charged dispersions of titanium dioxide, as are disclosed in U.S. Pat. No. 5,997,887.

Preferred colored or uncolored non-interference-type pigments have a primary average particle size of from 1 nm to 150,000 nm, more preferably from 10 nm to 5,000 nm, even more preferably from 20 nm to 1000 nm. Mixtures of the same or different pigment/powder having different particle sizes are also useful herein (e.g., incorporating a $TiO_2$ having a primary particle size of from about 100 nm to about 400 nm with a $TiO_2$ having a primary particle size of from about 10 nm to about 50 nm).

Interfacial Surface

The interfacial surface of the particle core can be either located directly on the surface of the particle core itself, or can be located one or more layers above the particle core if the particle core to be used is a coated particle core. When the particle core comprises a plurality of particles, the interfacial surface can extend over multiple particle surfaces.

Polymer

The first polymer, the second polymer, and/or the block co-polymer are attached to the particle core's interfacial surface at different points. As used herein, "attached" can include any suitable means of attachment, such as bonding (e.g., covalent, ionic), or adsorption (e.g., van der Waals, Hydrogen bonding, etc.) depending upon the desired final properties of the personal care composition.

In one embodiment, a block co-polymer is used. Polymers having the same or contrasting properties can be incorporated into a single block co-polymer. The block co-polymer can be attached to the core at single or multiple points.

The polymer(s) and/or block(s) have a chemical and/or physical property; at least one of these properties contrasts with the other(s). Examples of properties and corresponding contrasting properties can include, but are not limited to: hydrophobic and hydrophilic; acidic and basic; and anionic and cationic.

The contrasting properties of the polymer(s) and/or block(s) enable the resulting responsive particle to adapt to its environment. When there is a change in a parameter that affects a particular property, a first polymer's (or block's) property will be expressed, and the first polymer's (or block's) effect will be dominant over the second polymer's (or block's) contrasting property. For example, a change in solvent polarity could trigger a conformational change in the polymer chains, resulting in a more hydrophobic or hydrophilic property being expressed. Other changes could include pH, water content, humidity, temperature, solvent content, electrolyte concentration, magnetic field, radiation exposure, etc. In a particular embodiment, a polymer comprises not one but a plurality of properties such that it will be responsive to multiple stimuli (e.g., both solvent polarity and temperature.)

The inclusion of responsive particles in a personal care composition can thus lead to advantages such as, but not limited to, improved and uniform deposition of hydrophobic materials on hair or skin of non-uniform surface energies. For example, the deposition of these hydrophobic materials onto the hair surface changes the surface energy. This change in surface energy is typically measured by the water contact angle on the hair surface. In one embodiment, the change in hair contact angle is greater than 10 degrees, in another embodiment it is greater than 20 degrees, and in another embodiment, it is greater than 30 degrees, as measured by the method set forth in Example 33 herein. In another embodiment, the change in hair contact angle is in the range of from 10 degrees to 90 degrees, in another embodiment from 20 degrees to 90 degrees, and in another embodiment, from 30 degrees to 90 degrees, as measured by the method set forth in Example 33 herein.

Furthermore, formulation of hydrophobic materials into an aqueous chassis (e.g., dermatologically acceptable carrier) can be more easily accomplished. Conversely, the formulation of hydrophilic materials into a non-aqueous chassis can be more easily accomplished. In addition, the removal of the responsive particles can be facilitated by changes in environment.

The selection of the polymer types, levels, and ratios depends on the product type, desired property, stimulus, and chassis used. In general, it is desirable to be able to deliver the responsive particles in various chassis preserving their stability towards aggregation/flocculation and settling. For example, relatively large polymers may be selected to achieve entropic stabilization. In one embodiment, the polymer has a molecular weight of greater than 500, in another embodiment the molecular weight is more than 15,000. In a particular embodiment, the polymer has a molecular weight from 1000 to 300,000. In aqueous chassis, the presence of ionic groups in a hydrophilic polymer will provide additional flocculation/aggregation stability.

In particular embodiments, hydrophobic polymers can include, but are not limited to, fluorinated polystyrenes, polystyrenes, polyolefins (and functionalized, such as cyanides, halides, esters, pyrrolidone, carboxylic acids, carboxylic acid esters, hydroxyl, hydroxyl derivatives of carboxylic acid esters, amides, amines, glycidyl derivatives, etc.), polydienes, PDMS and functionalized PDMS, polybutylene oxides, polypropylene oxides, and alkyl derivatives and combinations thereof.

In particular embodiments, hydrophilic polymers can include, but are not limited to, polyacrylates (and esters), other functionalized polyolefins, (such as PVA (polyvinyl alcohols and esters), PVA ethers, PVP (vinyl pyrrolidones), vinyl cyanides, phosphates, phosphonates, sulfates, sulfonates, etc.), polyethylenimine and other polyamines, polyethylene glycols and other polyethers, poly(styrene maleic anhydride), polyesters, polyureas, polyurethanes, polycarbonates, polyacrylamides, sugars and polymeric analogs, chitosan, and derivatives thereof and combinations thereof.

In order to have a robust responsive behavior (rapid and effective switching behavior upon a stimulus) conformational flexibility of the polymers is important. Therefore, a low glass transition temperature is desirable.

When the attachment mechanism is adsorption, the presence of multiple particle affinity groups on the polymer may be advantageous in order to achieve effective attachment under the appropriate conditions.

Methods for Making Responsive Particle

In another aspect, the present invention provides methods for making responsive particles for use in personal care compositions. The method comprises: (1) providing a dermatologically acceptable particle having an interfacial surface, (2) attaching a first dermatologically acceptable polymer having a first property to said interfacial surface; and (3) attaching a second dermatologically polymer having a contrasting property to said interfacial surface.

In another embodiment, the method for making a responsive particle for use in personal care compositions comprises: (1) providing a dermatologically acceptable particle having an interfacial surface, (2) attaching at least one dermatologically acceptable block co-polymer comprising a first block and a second block to said interfacial surface, wherein said first block has a first property and said second block has a second property; and (3) optionally attaching at least one other dermatologically acceptable polymer having a third property to said interfacial surface, wherein at least one of the properties contrasts.

In general, the responsive particles can be prepared/manufactured by using existing particulate raw materials as pre-formed particle cores (pigments, filler, etc.) and reacting functional groups on their surface with polymers or, adsorbing polymeric materials on their surface (see Examples 1, 2, and 3). Alternatively, responsive particles can be manufactured as the result of a polymerization reaction of soluble/emulsifiable monomers or macromonomers. The resulting polymer/co-polymer will not only form the solid core but also the attached polymers that provide the responsive feature. Additionally, the polymerization may be performed in the presence of particles (e.g. inorganic pigment) that can serve as an additional core material.

The creation of responsive particles via polymerization reaction can provide a simple, fast, and economical process. For example, we can utilize aqueous emulsion polymerization of monomers containing at least one ethylene group in the presence of an initiator, a vinyl-terminated dimethylsiloxane macromonomer and, possibly, an alkene-containing polyethylenoxide. The silicone macromonomers can be emulsified into the aqueous medium with the other monomers using a surfactant in order to ascertain its participation to the polymerization reaction. After polymerization the resulting dispersion contains polymeric particles (latex) with attached macromonomers. Addition of inorganic particles (such as titanium dioxide, zinc oxide, silica etc) or other polymeric particles in the reaction mixture before the polymerization, also participate in the latex particles.

Typical emulsion polymerization monomers can include methyl methacrylate, acrylonitrile, ethyl acrylate, methacrylamide, styrene, etc. More hydrophilic monomers like acrylic acid and methacrylic acid may be copolymerized as well.

Examples of PDMS macromonomers can include vinyl-terminated polydimethylsiloxanes, vinylmethylsiloxane-dimethylsiloxane copolymers, methacroloxypropyl-terminated polydimethylsiloxanes, etc.

Examples of polar macromonomers can include polyoxyethylene esters of unsaturated fatty acid, polyoxyethylene ethers of fatty alcohols, vinyl-terminated polyethylenimine, 2-(dimethylamino) ethyl methacrylate, etc.

Similar results can be obtained when dispersion polymerization is attempted in an organic solvent instead of water. Typical solvents that can be used in this free radical dispersion polymerization include methylethyl ketone, isopropanol, etc.

In the case where an inorganic particle (such as titanium dioxide, zinc oxide, silica, etc) is used in the aqueous reaction mixture, encapsulation of the particle with an unsaturated fatty acid polyoxyethylene ester or fatty alcohol polyoxyethylene ether followed by reaction with PDMS macromonomer can be another approach of creating similar responsive structures.

Optional Components/Ingredients

The compositions of the present invention can comprise one or more suitable desired optional components. For example, the composition can optionally include other active or inactive ingredients. Compositions comprising a peptide in combination with an optional keratinous tissue active, such as niacinamide, can be capable of providing additive and/or synergistic keratinous tissue (e.g., skin, hair, or nail) benefits.

For instance, such materials can be selected from the group consisting of sugar amines (e.g., N-acetylglucosamine), vitamin B3 compounds, sodium dehydroacetate, dehydroacetic acid and its salts, phytosterols, soy derivatives (e.g., equol and other isoflavones), niacinamide, phytantriol, farnesol, bisabolol, salicylic acid compounds, hexamidines, dialkanoyl hydroxyproline compounds, flavonoids, N-acyl amino acid compounds, retinoids (e.g., retinyl propionate), water-soluble vitamins, ascorbates (e.g., vitamin C, ascorbic acid, ascorbyl glucoside, ascorbyl palmitate, magnesium ascorbyl phosphate, sodium ascorbyl phosphate), particulate materials, sunscreen actives, anti-cellulite agents, butylated hydroxytoluene, butylated hydroxyanisole, their derivatives, and combinations thereof.

Other examples of optional ingredients can include cationic polymers, conditioning agents (hydrocarbon oils, fatty esters, silicones), anti dandruff agents, antiseborrheic agents, antipsoriasis agents, oxidative dye precursors, developers, oxidizing agents, alkalizing agents, suspending agents, viscosity modifiers, dyes, nonvolatile solvents or diluents (water soluble and insoluble), pearlescent aids, foam boosters, surfactants, nonionic cosurfactants, pediculocides, pH adjusting agents, perfumes, preservatives, chelants, chelating agents, proteins, UV absorbers, pigments, other amino acids, and other vitamins.

For instance, the compositions of the present invention may comprise one or more vitamins and/or amino acids such as: water soluble vitamins such as vitamin B1, B2, B6, B12, C, pantothenic acid, pantothenyl ethyl ether, panthenol, biotin, and their derivatives, water soluble amino acids such as asparagine, alanine, glutamic acid and their salts, water insoluble vitamins such as vitamin A, D, E, and their derivatives, water insoluble amino acids such as tyrosine, tryptophan, and their salts.

The compositions of the present invention may also contain one or more pigment materials such as inorganic, nitroso, monoazo, disazo, carotenoid, triphenyl methane, triaryl methane, xanthene, quinoline, oxazine, azine, anthraquinone, indigoid, thionindigoid, quinacridone, phthalocyanine, botanical, natural colors, including: water soluble components such as those having C. I. Names. The compositions of the present invention may also contain antimicrobial agents which are useful as cosmetic biocides and antidandruff agents including: water soluble components such as piroctone olamine, water insoluble components such as 3,4,4'-trichloro-carbanilide (trichlosan), triclocarban and zinc pyrithione.

Furthermore, the composition can comprise other peptides, such as those disclosed in U.S. Pat. No. 6,492,326, issued Dec. 10, 2002, to Robinson et al. (e.g., pentapeptides such as lys-thr-thr-lys-ser, and derivatives thereof). Suitable pentapeptide derivatives include palmitoyl-lys-thr-thr-lys-ser, available from Sederma, France. Another optional dipeptide that can be used in the composition herein is carnosine. As used herein, the term "peptide" is broad enough to include one or more peptide, one or more peptide derivatives, and combinations thereof.

Any other suitable optional component can also be included in the personal care composition of the present invention, such as those ingredients that are conventionally used in given product types. The CTFA Cosmetic Ingredient Handbook, Tenth Edition (published by the Cosmetic, Toiletry, and Fragrance Association, Inc., Washington, D.C.) (2004) (hereinafter "CTFA"), describes a wide variety of nonlimiting materials that can be added to the composition herein. Examples of these ingredient classes include, but are not limited to: abrasives, absorbents, aesthetic components such as fragrances, pigments, colorings/colorants, essential oils, skin sensates, astringents, etc. (e.g., clove oil, menthol, camphor, eucalyptus oil, eugenol, menthyl lactate, witch hazel distillate), anti-acne agents, anti-caking agents, anti-foaming agents, antimicrobial agents (e.g., iodopropyl butyl-carbamate), antibacterial agents, antifungal agents, antioxidants, binders, biological additives, buffering agents, bulking agents, chelating agents, chemical additives, colorants, cosmetic astringents, cosmetic biocides, denaturants, drug astringents, external analgesics, film formers or materials, e.g., polymers, for aiding the film-forming properties and substantivity of the composition (e.g., copolymer of eicosene and vinyl pyrrolidone), opacifying agents, pH adjusters, plant derivatives, plant extracts, plant tissue extracts, plant seed extracts, plant oils, botanicals, botanical extracts, preservatives, propellants, reducing agents, sebum control agents, sequestrants, skin bleaching and lightening agents, (e.g. hydroquinone, kojic acid, ascorbic acid, magnesium ascorbyl phosphate, ascorbyl glucoside, pyridoxine), enzymes, coenzymes, skin-conditioning agents (e.g. humectants and occlusive agents), skin soothing and/or healing agents and derivatives (e.g. panthenol, and derivatives such as ethyl panthenol, aloe vera, pantothenic acid and its derivatives, allantoin, bisabolol, and dipotassium glycyrrhizinate), skin treating agents (e.g. vitamin D compounds, mono-, di-, and tri-terpenoids, beta-ionol, cedrol), thickeners, rheology modifiers, and vitamins and derivatives thereof.

Although the previous components were discussed in terms of their use as optional ingredients, it should be evident to one skilled in the art that many of these components could also be suitably used as components of the core and/or polymer of the responsive particles of the present invention.

Carrier

The compositions of the present invention comprise a dermatologically acceptable carrier. The carrier can be in a wide variety of forms. Non-limiting examples include simple solutions or dispersions (e.g., water, oil, or hydrocarbon based), emulsions, solid forms (gels, sticks), and substrates.

Composition Preparation

The compositions useful for the methods of the present invention are generally prepared by conventional methods such as are known in the art of making topical compositions. Such methods typically can involve mixing of the ingredients in one or more steps to a relatively uniform state, with or without heating, cooling, application of vacuum, and the like.

EXAMPLES

The following are non-limiting examples of compositions of the present invention. The examples are given solely for the purpose of illustration and are not to be construed as limitations of the present invention, as many variations thereof are possible without departing from the spirit and scope of the invention, which would be recognized by one of ordinary skill in the art.

In the examples, all concentrations are listed as weight percent, unless otherwise specified and may exclude minor materials such as diluents, filler, and so forth. The listed formulations, therefore, comprise the listed components and any minor materials associated with such components. As is apparent to one of ordinary skill in the art, the selection of these minors will vary depending on the physical and chemical characteristics of the particular ingredients selected to make the present invention as described herein.

Example 1

Preparation of Grafted Micronized Titanium Dioxide Using Sonicator

A. Reaction of Titanium Dioxide with (3-Glycidopropyl) Trimethylsilane

A suspension of 5.0 g titanium dioxide (Aeroxide® P25; supplied by Degussa) in 500 ml methylethyl ketone (MEK) stored over molecular sieves 4A, 4-8 mesh (supplied by Sigma-Aldrich) is prepared in a high speed mixer (Silverson® L4RT) for 30 minutes using a rotor-stator adaptor at 1000 rpm. Then, 10 grams of (3-glycidopropyl) trimethylsilane (supplied by Gelest Inc; product code SIG5840.0) are added and the mixture is sonicated for 10 hours using a Branson 5210 sonicator bath. The dispersion is ultracentrifuged (20,000 rpm for 1 hour) using Sorvall RC 26 Plus Ultracentrifuge with SS-34 rotor, the supernatant liquid is decanted and the paste washed three times with fresh MEK in order to remove unreacted reagent and other impurities. Washing includes sonication for 5 minutes, ultracentrifugation (20,000 rpm for 30 minutes), decanting of the supernatant liquid and addition of more fresh solvent.

B. Polydimethylsiloxane Grafting

The washed paste is diluted with 100 ml MEK and mixed with a solution containing 150 ml MEK and 250.0 g aminopropyl-terminated polydimethylsiloxane (MW 30,000; supplied by Gelest Inc; product code DMS-A32). The resulting dispersion is sonicated for 20 hours at room temperature (Branson 5210 sonicator bath). The mixture is ultracentrifuged and washed three times with fresh MEK as described above.

C. Polyethylenimine Grafting

The washed paste is mixed with 100 ml MEK. A solution containing 150 ml MEK and 250.0 g polyethylenimine (MW ~25,000 [MW=molecular weight]; supplied by Sigma-Aldrich; product code 408727; CAS 9002-98-6) is added into the dispersion and the mixture is sonicated for 20 hours at room temperature. Then, the dispersion is ultracentrifuged and washed three times with fresh solvent as described above. The washed paste is washed twice with 500 ml millipore water and diluted with millipore water to a final dispersion containing 1% solids by weight.

Example 2

Preparation of Grafted Pigment Grade Titanium Dioxide Using Sonicator

The procedure of Example 1 is repeated using a pigment-grade titanium dioxide (Tronox® CR-840; supplied by Tronox Incorporated) instead of the nanoparticulate Aeroxide® P25 titanium dioxide.

Example 3

Preparation of Grafted Micronized Titanium Dioxide Using Agitated Bead Mill

The procedure of Example 1 is repeated using the same materials as in Example 1. All reaction steps are performed in an agitated bead mill such as Netzsch® LMZ0.3 that contains 200 ml of ytterbium oxide stabilized zirconium dioxide media (YTZ® manufactured by Tosho; spheres with diameter of 0.40 mm). The mill is run at high rotation per minute (2,500-3,000). This procedure contributes to particle de-aggregation/de-agglomeration and avoids grafting of large particle aggregates. In general, smaller particles are not only more effective in treating substrate surfaces (less quantity needed) but they also contribute to reduced side-effects such as rough "feel", and reduced shine. The reactions can be also performed in other size reducing equipment such as sonication gun such as Branson Sonifier 250, rotor-stator-mill such as Silverton® L4RT, attritor such as UPA 01 HD, rotating ball mill, sonolator, sigma-blade kneader, etc.

Other Preparation Schemes

Simpler and faster reaction schemes may be used to prepare responsive nanoparticles more economically. For example, we can utilize aqueous emulsion polymerization of monomers containing at least one ethylene group in the presence of an initiator, a vinyl-terminated dimethylsiloxane macromonomer and, possibly, an alkene-containing polyethylenoxide. The silicone macromonomers can be emulsified into the aqueous medium with the other monomers using a surfactant in order to ascertain its participation to the polymerization reaction. After polymerization the resulting dispersion contains polymeric particles (latex) with attached macromonomers. Addition of inorganic particles (such as titanium dioxide, zinc oxide, silica etc) or other polymeric particles in the reaction mixture before the polymerization, also participate in the latex particles.

Typical emulsion polymerization monomers can include methyl methacrylate, acrylonitrile, ethyl acrylate, methacrylamide, styrene, etc. More hydrophilic monomers like acrylic acid and methacrylic acid may be copolymerized as well.

Examples of PDMS macromonomers can include vinyl-terminated polydimethylsiloxanes, vinylmethylsiloxane-dimethylsiloxane copolymers, methacroloxypropyl-terminated polydimethylsiloxanes, etc.

Examples of polar macromonomers can include polyoxyethylene esters of unsaturated fatty acid, polyoxyethylene ethers of fatty alcohols, vinyl-terminated polyethylenimine, 2-(dimethylamino) ethyl methacrylate, etc.

Similar results can be obtained when dispersion polymerization is attempted in an organic solvent instead of water. Typical solvents that can be used in this free radical dispersion polymerization include methylethyl ketone, isopropanol, etc.

In the case where an inorganic particle (such as titanium dioxide, zinc oxide, silica, etc) is used in the aqueous reaction mixture, encapsulation of the particle with an unsaturated fatty acid polyoxyethylene ester or fatty alcohol polyoxyethylene ether followed by reaction with PDMS macromonomer can be another approach of creating similar responsive structures.

Example 4

Preparation of Aqueous Dispersion of Micronized Titanium Dioxide

Into 100 ml water, 10.0 g of titanium dioxide (Aeroxide® P25; supplied by Degussa; primary particle size 21 nanometers) are added and dispersed for 3 hours using a high speed mixer (or a sonicator).

Example 5

Preparation of Aqueous Dispersion of Micronized Grafted Titanium Dioxide

The procedure of Example 4 is repeated using air-dried particles from Example 1 instead of Aeroxide® P25.

Example 6

Aqueous Dispersion Quality and Stability of Micronized Titanium Dioxide

The two dispersions from Examples 4 and 5 are compared for particle size, settling stability, and transparency. Dispersion from Example 5 shows smaller particle size (via light scattering measurement; Horiba LA-910), higher dispersion stability (very slow settling by observation of settling in a glass vial), and higher transparency than dispersion from Example 4. In order to measure transparency, a draw-down film is prepared of two dispersions (from Example 5 and Example 4) side-by-side on a Leneta card Form 5DX using a 1-mil Bird applicator (film draw down bar). After drying, transparency differences are assessed either by observation of the films or by measuring contrast ratios for the two films. More opaque material covers the black substrate more than the transparent material. Contrast ratio is the ratio of tristimulus value Y over the black part of the Leneta card and the tristimulus value Y over the white part of the Leneta card. Tristimulus values are measured with a Microflush® Color Computer (by Datacolor International). Smaller contrast ratio indicates higher transparency (lower opacity). Film from dispersion prepared from particles from Example 5, shows higher transparency. These observations suggest that grafted particles prepared in Example 1 are easily dispersible and stable in water media.

This is a result of the steric and electrostatic stabilization from the hydrophilic grafted polymer (polyethylenimine) on the titanium dioxide particles prepared in Example 1. Particles cannot come close to each other and aggregate and/or flocculate because of the electrostatic repulsion of the positively charges nitrogen atoms in polyethylenimine (PEI) as well as the entropic stabilization achieved by the extension of the polymeric PEI chains in the water medium. The same cannot be achieved in the dispersion that corresponds to the ungrafted Aeroxide® P25 particles (from Example 4).

Example 7

Preparation of Silicone Dispersion of Micronized Titanium Dioxide

The procedure of Example 4 is repeated using Aeroxideg® P25 but replacing the water medium with silicone fluid D5 (decamethyl cyclopentasiloxane) medium.

Example 8

Preparation of Silicone Dispersion of Micronized Grafted Titanium Dioxide

The procedure of Example 7 is repeated using air-dried particles from Example 1 instead of Aeroxide® P25 and using silicone fluid D5 decamethyl cyclopentasiloxane instead of water.

Example 9

Dispersion Quality and Stability of Micrinized Titanium Dioxide in Silicone Fluid The two dispersions from Examples 7 and 8 are compared for particle size, settling stability, and transparency. Dispersion from Example 8 shows smaller particle size (via light scattering measurement; Horiba LA-910), higher dispersion stability (very slow settling by observation of settling in a glass vial), and higher transparency than dispersion from Example 7. The same methodologies are utilized for these comparisons as described in the section for "Aqueous Dispersion Quality and Stability" (see above). The grafted particles prepared in Example 1 are not only dispersible and stable in aqueous medium (see Example 6), but also in hydrophobic silicone fluids. This is a result of the steric stabilization from the hydrophobic grafted polymer (polydimethylsiloxane PDMS) on the titanium dioxide particles prepared in Example 1. Particles cannot come close to each other and aggregate and/or flocculate because of the entropic stabilization achieved by the extension of the polymeric PDMS chains in the water medium. The same cannot be achieved in the dispersion that corresponds to the ungrafted Aeroxide® P25 particles (from Example 8).

Example 10

Preparation of Castor Oil Dispersion of Pigment Grade Grafted Titanium Dioxide Air-dried grafted pigment-grade titanium dioxide particles from Example 2 (10 g) are dispersed in 500 g of castor oil using a high speed mixer (Silverson® L4RT) for 30 minutes using a rotor-stator adaptor at 1000 rpm. Dispersions of the same particle concentration are also prepared in various vehicles such as water, silicone fluid D5 (decamethyl cyclopentasiloxane), and mineral oil. Particle size measurement of all three dispersions via light scattering (Horiba LA-910) indicates very similar average particle size suggesting that grafted pigment is well-dispersible and compatible in all these media. This suggests that grafted pigment particles are dispersible and stable in media of various nature and polarities. This fact combined with the observation that stability does not depend on the addition of other dispersants and/or surfactants makes formulation of these particles very simple. Therefore, they can be used as universal opacifying materials that can work in a variety of color cosmetic and other chassis.

Example 11

Preparation of Concentrated Castor Oil Dispersion of Pigment Grade Grafted Titanium Dioxide Air-dried grafted pigment-grade titanium dioxide particles from Example 2 (100.0 g) are dispersed in 300.0 g of castor oil using an agitated bead media mill (Netzsch® LMZ0.3)

that contains 200 ml of ytterbium oxide stabilized zirconium dioxide media (YTZ® manufactured by Tosho; spheres with diameter of 0.40 mm). The mill is run at high rotation per minute (2,500-3,000) for 6 hours or until a fineness-of-grind rating of 6 (Hegman Scale) is achieved. For this determination a stainless steel Fineness of Grind Gage is used (block size ¾×2½×8; path size ½×6; range in Hegman scale 0-8) supplied by Gardco (item 65).

Example 12

Preparation of Lipstick from Concentrated Caster Oil Dispersion of Pigment Grade Titanium Dioxide The dispersion from Example 11 is used for the preparation of wax-based short term lipstick. The lipstick contains 3% grafted titanium dioxide (from Example 2, 10% D&C Pigment Red 7 castor oil dispersion containing 35% pigment (Product code COD-8001) supplied by SunChemical Corporation), and 80% lipstick base containing castor oil, wax thickeners and other additives (see composition below). The lipstick preparation includes gently mixing of all ingredients with a spatula at a temperature of 75° C. and filling up a pre-heated lipstick mold with the resulting melt. Lipsticks are solidified by the insertion of the mold in a freezer (−15° C.) for 1 hour.
Composition of Lipstick Base

| Material | % By weight |
| --- | --- |
| Isopropyl isostearate | 41.0 |
| Octyl hydroxystearate | 16.0 |
| Acetylated Lanolin | 15.0 |
| Ozokerite wax SP-1026P | 8.0 |
| Candelilla Wax 65C SP-75 | 5.0 |
| Paraffin Wax 62C SP-673P | 3.0 |
| Carnauba wax #1 Flakes NF SP-63 | 5.0 |
| Cetyl Alcohol 95% | 6.8 |
| Propylparaben | 0.2 |

Example 13

Preparation of Concentrated Caster Oil Dispersion of Pigment Grade Titanium Dioxide The preparation described in Example 11 is repeated using 100 g of standard titanium dioxide pigment powder such as Tronox® CR-840 (instead of grafted particles from Example 2) dispersed in 300.0 g of castor oil.

Example 14

Preparation of Lipstick from Concentrated Castor Oil Dispersion of Pigment Grade Titanium Dioxide The preparation of lipsticks described in Example 12 is repeated using the castor oil dispersion from in Example 13 instead of dispersion from Example 11.

Example 15

Comparison of Lipsticks

Lipsticks from Examples 13 and 14 are separately mixed with a spatula to a fluid dispersion. Then, side-by side films are prepared on black and white Leneta card Form 5DX using a 1-mil Bird applicator (film draw down bar). The two films are similar in color shade and transparency, assessed by observation or measured with Microflash color computer (by Datacolor International), as well as gloss, measured with a Byk-Gartner Micro TRI gloss meter.

Example 16

Properties of Castor Oil Dispersions

A mixture containing 99 parts of the dispersion prepared in Example 11 and 1 part of D&C Pigment Red 7 dispersion in castor oil (Product code COD-8001 supplied by SunChemical Corporation) is prepared. Similarly, a mixture containing 99 parts of the dispersion prepared in Example 13 and 1 part of D&C Pigment Red 7 dispersion in castor oil (Product code COD-8001 supplied by SunChemical Corporation) is prepared. A side-by-side draw-down of the two mixtures on a Leneta card Form 5DX with a 1-mil Bird applicator (film draw down bar) is also prepared. Measurement of the color strength of these two films by Microflash color computer (by Datacolor) or assessed by observation of the films shows that they have similar color strength and shade.

Example 17

Preparation of Silicone Dispersion of Pigment Grade Grafted Titanium Dioxide

Air-dried grafted pigment particles from Example 2 (60 g) are dispersed in 200 g of D5 silicone fluid (decamethyl cyclopentasiloxane) using an agitated media mill such as Netzsch® LMZ0.3 (for process details see Example 3).

Example 18

Preparation of Silicone Dispersion of Pigment Grade Titanium Dioxide

Silicone-treated titanium dioxide pigment (60 g; Product Code: RBTD-TTB2 supplied by Kobo Products; INCI name: Titanium Dioxide (And) Triethoxysilylethyl Polydimethylsiloxyethyl Methicone) is also dispersed 200 g of D5 silicone fluid (decamethyl cyclopentasiloxane) an agitated media mill such as Netzsch® LMZ0.3 (for process details see Example 3).

Example 19

Preparation of Silicone Dispersion of Pigment Grade Red Iron Oxide

Silicone-treated red iron oxide pigment 60 g; Product Code: BGRO-TTB2 supplied by Kobo Products; INCI name: Iron Oxide (And) Triethoxysilylethyl Polydimethylsiloxyethyl Methicone) is also dispersed 200 g of D5 silicone fluid (decamethyl cyclopentasiloxane) an agitated media mill such as Netzsch® LMZ0.3 (for process details see Example 3).

Example 20

Preparation of Silicone Dispersion of Pigment Grade Yellow Iron Oxide

Silicone-treated yellow iron oxide pigment (60 g; Product Code: BGYO-TTB2 supplied by Kobo Products; INCI name: Iron Oxide (And) Triethoxysilylethyl Polydimethylsiloxyethyl Methicone) is also dispersed 200 g of D5 silicone fluid (decamethyl cyclopentasiloxane) an agitated media mill such as Netzsch® LMZ0.3 (for process details see Example 3).

Example 21

Preparation of Silicone Dispersion of Pigment Grade BLACK Iron Oxide

Silicone-treated red iron oxide pigment (60 g; Product Code: BGBO-TTB2 supplied by Kobo Products; INCI name: Iron Oxide (And) Triethoxysilylethyl Polydimethylsiloxyethyl Methicone) is also dispersed 200 g of D5 silicone fluid (decamethyl cyclopentasiloxane) an agitated media mill such as Netzsch® LMZ0.3 (for process details see Example 3).

Example 22

Preparation of Silicone Dispersion of Pigment Grade Red Iron Oxide

Silicone-treated red iron oxide pigment (60 g; Product Code: RBRO-TTB2 supplied by Kobo Products; INCI name: Iron Oxide (And) Triethoxysilylethyl Polydimethylsiloxyethyl Methicone) is also dispersed 200 g of D5 silicone fluid (decamethyl cyclopentasiloxane) an agitated media mill such as Netzsch® LMZ0.3 (for process details please see Example 3).

Example 23

Preparation of Mixture of Silicone Dispersion of Pigment Titanium Dioxide (Example 17) and Red Iron Oxide A mixture of 9.9 g of the dispersion prepared in Example 17 and 0.1 g of the dispersion prepared in Example 19 is prepared. The mixture is agitated with a spatula until uniform.

Example 24

Preparation of Mixture of Silicone Dispersion of Pigment Titanium Dioxide (Example 18) and Red Iron Oxide A mixture of 9.9 g of the dispersion prepared in Example 18 and 0.1 g of the dispersion prepared in Example 19 is prepared. The mixture is agitated with a spatula until uniform.

Example 25

Properties of Silicone Dispersions

Dispersions prepared in Example 17 and Example 18 are diluted with decamethyl cyclopentasiloxane to particle concentration of 5% and drawn down side-by-side on a Leneta card Form 5DX with a 1-mil Bird applicator (film draw down bar). The two films show similar shade, transparency, and gloss by observation of the wet film and by measurements of the fresh film using Microflash color computer (by Datacolor) and Byk-Gartner Micro TRI gloss meter.

The dispersion mixture from Example 23 is drawn-down side-by-side to the dispersion mixture from Example 24 on a Leneta card Form 5DX with a 1-mil Bird applicator (film draw down bar). Observation of the wet films of the two mixtures shows that the two dispersions are similar in color shade, color strength and transparency.

The films of Example 25b are allowed to dry completely and compared again. New observation shows that dry film of the dispersion corresponding to Example 23 is more opaque and shows lower color strength than dry film of the dispersion corresponding to Example 24 (and similar to wet film corresponding to Example 23). Therefore, there is a shift in lower opacity and higher color strength of film from Example 24 during drying. This is an indication of instability of the methicone-treated titanium dioxide pigment particles during drying, something that is not observed with the grafted particles from Example 2. Therefore, the responsive nature of these particles contribute to dispersion stability at media of various polarities.

Example 26

Preparation of Liquid Foundation (Emulsion with Silicone External Phase) using Dispersion from Example 17

A liquid foundation with the following composition and process is prepared using titanium dioxide dispersion prepared in Example 17:

| Ingredient | Wt % |
| --- | --- |
| Decamethyl cyclopentasiloxane | 11.62% |
| Dimethicone copolyol emulsifier | 0.70% |
| KSG32 Elastomer Gel | 5.38% |
| (25% Lauryl dimethicone/copolyol crosspolymer in isododecane) | |
| GE SFE839 Elastomer Gel | 10.00% |
| (5% Dimethicone/Vinyl Dimethicone crosspolymer) | |
| Isononyl Isononanoate | 5.00% |
| n-Propyl-4-hydroxybenzoic Acid | 0.20% |
| Ethylene Brassylate | 0.03% |
| Titanium Dioxide dispersion (Example 17) | 17.80% |
| Yellow Iron Oxide dispersion (Example 20) | 1.70% |
| Red Iron Oxide dispersion (Example 22) | 0.19% |
| Black Iron Oxide dispersion (Example 21) | 0.11% |
| Methylparahydroxybenzoate | 0.10% |
| Glycerine | 10.00% |
| 2-Amino-2-methyl-1-propanol | 0.10% |
| Water | 36.45% |
| Sucrose oleate ester | 0.60% |

In a stainless steel vessel, the decamethyl cyclopentasiloxane, dimethicone copolyol, GE SFE839, KSG32, isononyl isononanoate, n-propyl-4-hydroxybenzoic acid, and ethylene brassylate are added with mixing using a high speed mixer (Silverson® L4RT) for 30 minutes using a rotor-stator adaptor at 1000 rpm and mixed until uniform. In a separate vessel equipped with a heat source, the sucrose oleate ester and water are heated to 50° C. and similarly mixed until uniform. The sucrose oleate ester mixture is then allowed to cool to room temperature. Once cooled, the titanium dioxide, iron oxides, methylparahydroxy benzoate, glycerine and 2-amino-2-methyl-1-propanol are added to sucrose oleate ester mixture with mixing to form a uniform pigment slurry. Then, the sucrose oleate ester mixture is combined with the decamethyl cyclopentasiloxane mixture and mixed (as above) until uniform. The combined mixture is then poured into suitable containers.

Example 27

Preparation of Liquid Foundation (Emulsion with Silicone External Phase) using Dispersion from Example 18

The preparation of liquid foundation as described in Example 26 is repeated replacing the titanium dioxide dispersion prepared in Example 17 with the titanium dioxide dispersion prepared in Example 18.

Example 28

Properties of Liquid Foundations

A panel study with 10 panelists is performed in order to determine properties of foundations from Examples 27 and 28. Panelists express preference for liquid foundation from example 27 for the following reasons:
 a. Less shade and transparency shift upon drying
 b. Better coverage
 c. Decreased appearance of skin texture (pores, wrinkles)
 d. Ease of removal using a wet wipe.

Example 29

Preparation of Liquid Foundation (Emulsion with Water as the External Phase)

A liquid foundation with the following composition and process is prepared using titanium dioxide dispersion prepared in Example 2 (dried):

Into a stainless steel vessel, 8.50 g of isopropyl myristate, 5.66 g of mineral oil, 3.15 g of cetyl palmitate, 2.45 g of glyceryl monostearate, 1.70 g of stearic acid, 0.10 g of sodium stearate, and 0.10 g of propylparaben are added and mix at 70° C. using a high speed mixer (Silverson® L4RT) using a rotor-stator adaptor at 1000 rpm until uniform. Then, pigments are added as follows: 9.94 g of titanium dioxide from Example 1 (dried), 2.18 g of yellow iron oxide, 1.12 g of red iron oxide, and 0.56 g black iron oxide. The dispersion is mixed in a high speed mixer (Silversong® L4RT) for 60 minutes using a rotor-stator adaptor at 1000 rpm at 70° C. (Phase A). In a separate vessel 29.64 g of deionized water, 9.72 g of propylene glycol and 0.21 g of methylparaben are added and mixed for 5 minutes at 70° C. as above. A mixture of 0.25 g of carboxymethyl cellulose and 3.08 g of propylene glycol are added followed by addition of a solution containing 0.72 g of sodium lauryl sulfate and 0.76 g of triethanolamine in 1.76 g water under agitation (Phase B). Phase A is added into Phase B under agitation and then a dispersion of 0.70 g talc in 17.70 g water are added to the mixture. The mixture is then poured into suitable containers.

Example 30

Preparation of Mascara (Emulsion with Water as the External Phase) Containing Grafted Titanium Dioxide from Example 1

A mascara with the following composition and process is prepared using titanium dioxide dispersion prepared in Example 1 (dried):

| Ingredient | % by wt |
| --- | --- |
| Vinyl acetate/vinyl pyrrolidone copolymer (Copolymer W-735 supplied by ISP) | 38.00% |
| Deionized water | 24.50% |
| Paraffin wax | 7.00% |
| Stearic acid | 9.00% |
| Triethanolamine | 1.50% |
| Dried titanium dioxide from Example 1 | 1.50% |
| Black iron oxide | 8.50% |
| Syntran 5170 (ammonium acrylates copolymer emulsion Supplied by Inetrpolymer Corp.) | 10.00% |

The wax and fatty acid are added into a vessel equipped with heating and mixing. The temperature is raised to 85° C. and the ingredients are mixed to a homogeneous liquid in a high speed mixer (Silverson® L4RT) using a rotor-stator adaptor at 300 rpm. Then, the black iron oxide pigment is added and mixed for 60 minutes at 1000 rpm to disperse. In a second vessel equipped with mixing and heating, the water, triethanolamine and titanium dioxide are added and mixed in a high speed mixer (Silverson® L4RT) for 30 minutes using a rotor-stator adaptor at 300 rpm at 85° C. The two phases are combined slowly and mixed using a in a high speed mixer (Silverson® L4RT) for 30 minutes using a rotor-stator adaptor at 1000 rpm. Then, the ammonium acrylate copolymer emulsion is added and similarly mixed (at 300 rpm) until uniform. Gentle mixing is continued and heat source is removed to cool emulsion to approximately 30° C.

Example 31

Preparation of Mascara (Emulsion with Water as the External Phase)

The preparation of mascara described in Example 30 is repeated without the addition of grafted titanium dioxide particles.

Example 32

Evaluation of Water-Based Mascara

Mascara prepared in Examples 30 and 31 is applied to artificial eyelashes and the corresponding films are observed using an optical microscope. Film from example 30 appears more strongly attached to the substrate and more uniform.

Example 33

Treatment of Bleached Hair with Grafted Titanium Dioxide Particles

Grafted titanium dioxide particles prepared in Example 1 are dispersed in water with a high speed mixer (Silverson® L4RT) for 30 minutes using a rotor-stator adaptor at 1000 rpm (pigment concentration 1% by weight). A 4.0-gram switch of bleached hair (length 6 inches) is treated with 2.0 ml of this aqueous dispersion diluted to a concentration of 0.04% by weight. The hair switch is left to dry at room temperature. The contact angle of the treated switch (approx. 10 hair fibers) are tested for contact angle by the Dynamic Absorbancy Test (see method below). After 1 minute the contact angle is 105 degrees and it is relatively stable for the duration of the measurement. Similar contact angles are measured at ten different places of the hair arrangement, indicating uniform deposition of the particles. The same test on control bleached hair shows contact angle of 65 degrees. Virgin (not chemically treated) hair shows contact angle of approximately 95-100 degrees. This indicates that grafted titanium dioxide particles transform oxidized hair from hydrophilic to hydrophobic.

Hair Contact Angle Determination Method

Approximately 0.5 grams of hair is spread evenly over a rectangular (2 cm×20 cm×1 cm) stage and attached at both ends with small clips. This stage is guided into the Dynamic Absorbancy Tester (Fibro DAT Model 1121, manufactured by Fibro Co.) so that the stage and hair sample are aligned with a high speed camera. A drop of a specified volume of water or other liquid is automatically applied to the test specimen by the instrument under specified deposition parameters. In our testing, 4 microliters of water was used. Images of the drop in contact with the substrate are captured by a video camera at specified time intervals (millisecond). The contact angle between the drop and substrate at various time intervals are determined by image analysis techniques on captured images, and the contact angle at specified times, the rate of change in the contact angle as a function of time, and changes in the droplet height and diameter are analyzed. The instrument can be set to take multiple measurements of the spreading and contact angle over time of 0.4 microliter droplet of water.

Responsive titanium dioxide grafted particles prepared in Example 1 are dispersible in water. In an aqueous environment, polydimethylsiloxane (PDMS) chain is coiled and polyethylenimine (PEI) chain is extended providing steric and electrostatic particle stabilization towards aggregation (see also note on Example 6). Upon drying, the opposite is happening (PEI coiling and PDMS extending) exposing the PDMS surface on the hair surface and increasing hydrophobicity of hair (as well as its contact angle).

Example 34

Preparation of Conditioning Shampoo Containing Grafted Particles from Example 1

Shampoo formulations containing the following ingredients are prepared.

| Component | Shampoo 34A wt % | Shampoo 34B wt % | Shampoo 34C wt % | Shampoo 34D wt % |
|---|---|---|---|---|
| Water | QS | QS | QS | QS |
| Polyquaternium 10 (Ucare Polymer LR-400) | 0.5 | 0.5 | 0.5 | 0.5 |
| Coconut monoethanolamide (Monamid CMA) | 1.5 | 1.5 | 1.5 | 1.5 |
| Disodium EDTA (Disslovine Na2S) | 0.0991 | 0.0991 | 0.0991 | 0.0991 |
| Sodium Benzoate (Purox S Grains) | 0.25 | 0.25 | 0.25 | 0.25 |
| Sodium Citrate Dihydrate | 0.452 | 0.452 | 0.452 | 0.452 |
| Citric Acid | 0.04 | 0.04 | 0.04 | 0.04 |
| Sodium Chloride | 0.0145 | 0.0145 | 0.0145 | 0.0145 |
| Dimethicone (Viscasil 3000,000) | — | — | 1.351 | 1.351 |
| Ammonium Laureth-3-Sulfate (AE3S) | 6 | 6 | 6 | 6 |
| Ethylene glycol distearate (EGDS) | 1.5 | 1.5 | 1.5 | 1.5 |
| Ammonium Lauryl Sulfate (ALS) | 10 | 10 | 10 | 10 |
| Methylchloroisothiazolinone & Methylisothiazolinone (Kathon CG) | 0.0005 | 0.0005 | 0.0005 | 0.0005 |
| Fragrance | 0.7 | 0.7 | 0.7 | 0.7 |
| PEG 7M (Polyox WSR-N-750) | 0.1 | 0.1 | 0.1 | 0.1 |
| DL Panthenol 50% soln. (DL-Panthenol 50L) | 0.03 | 0.03 | 0.03 | 0.03 |
| DL Panthenyl Ethyl Ether (Pantyl Ethyl Ether) | 0.03 | 0.03 | 0.03 | 0.03 |
| Lysine Monochloride | 0.028 | 0.028 | 0.028 | 0.028 |
| L-Tyrosine Methylester Hydrochloride (Methyl Tyrosine) | 0.0138 | 0.0138 | 0.0138 | 0.0138 |
| Histidine | 0.008 | 0.008 | 0.008 | 0.008 |
| Cetyl Alcohol | 0.9 | 0.9 | 0.9 | 0.9 |
| Particles from Example 1 | 0 | 1.351 | 0 | 1.351 |

Preparation Process

The water along with the surfactants and any solids that need to be melted are mixed in a high speed mixer (Silversong® L4RT) using a rotor-stator adaptor at 300 rpm at elevated temperature (72° C.) for 30 minutes and then the mixture is cooled to room temperature. Additional ingredients, including electrolytes, polymers, and particles are added to this cooled mixture under agitation. The silicone is emulsified at room temperature in concentrated surfactant and also added to the cooled product.

Example 36

Conditioning Shampoo Application and Evaluation Application

A hair switch consisting of 15.0 g of bleached hair is thoroughly wetted with a water stream at temperature of 37° C. and flow of 1.5 grams per minute. A quantity of 0.75 ml of the shampoo from Example 34A is applied to each side of the switch and massaged for 30 seconds followed by rinsing for another 30 seconds. Shampoo application and rinsing is repeated. The switch is allowed to dry overnight. The same protocol is applied for the shampoos prepared in Examples 34B, 34C, and 34D. Also, all four shampoo products are tested on hair switches consisting of virgin hair. Contact angle (CA) determination of dried hair switches (see method described in Example 33) were performed. The following table summarizes results.

| SHAMPOO | VIRGIN HAIR | BLEACHED HAIR |
|---|---|---|
| Example 34A | High CA | Low CA |
| Example 34B | High CA | High CA |
| Example 34C | High CA | Medium CA |
| Example 34D | High CA | High CA |

Example 37

Preparation of Hair Conditioner (Rinse-Off) with Grafted Particles from Example 1

A conditioner formulation containing the following ingredients is prepared.

| Ingredient | % by weight |
|---|---|
| Dow Corning Fluid 345 | 7.00% |
| Polyvinyl isobutyl ether (Lutonal IC 115 supplied by BASF) | 0.02% |
| Corn Starch powder (supplied by CPC International) | 3.50% |
| Stearyl benzyl dimethyl ammonium chloride | 0.30% |
| Ethanol | 7.00% |
| Titanium dioxide grafted particles from Example 1 (concentration adjusted to 10%) | 10% |
| Deionized water | balance |

Preparation Process

This conditioner is prepared by dissolving 35.0 g of the starch powder in 822 g of deionized water with a high speed mixer (Silverson® L4RT) using a rotor-stator adaptor at 300 rpm at elevated temperature (65° C.) for 60 minutes. Then 3.0 g of the stearyl benzyl dimethyl ammonium chloride are added followed by a solutioin of 0.2 g Lutonal IC 115 in 70 g of Dow Corning fluid 345. The speed of the mixer in increased to 1000 rpm and the mixture is sheared until particle size is decreased below 10 micrometers. Then, 70 g of ethanol are added along with 100 g of the titanium dioxide grafted particle dispersion. The mixture is finally cooled to room temperature.

Example 38

Preparation of Hair Conditioner (Rinse-Off) without Grafted Particles

The preparation of the conditioner formulation described in Example 37 is repeated without the addition of titanium dioxide grafted particles (replaced with water).

Example 39

Hair Conditioner Application and Evaluation
Application

A hair switch consisting of 15.0 g of bleached hair is thoroughly wetted with a water stream at temperature of 37° C. and flow of 1.5 grams per minute. A quantity of 0.75 ml of a standard shampoo is applied to each side of the switch and massaged for 30 seconds followed by rinsing for another 30 seconds. Shampoo application and rinsing is repeated. The switch is then treated with 0.75 ml of the conditioner, followed by massaging into hair for 30 seconds, waiting for 30 seconds, and rinsing for 30 seconds. The switch is then allowed to dry overnight. The procedure is repeated using switch consisting of virgin hair.
Hair Surface Evaluation Contact angle (CA) of the dried switches is measured at 10 different position by method described in Example 33. In addition, SEM images are also collected in order to determine uniformity of particle distribution. Particles of conditioner prepared in Example 37 are evenly distributed throughout the hair switches. All hair switches are found to be hydrophobic, but contact angle of hair switches treated with conditioner of Example 37 are more hydrophobic (higher contact angle; similar to contact angle of treated and untreated virgin hair).
UV Damage Evaluation Dried treated switches are inserted in a device that simulates sun exposure for 15 hours (Atlas Ci-3000+Fade-ometer; irradiance of 1.48 W/m$^2$ at wavelength of 420 nm; relative humidity 80%). Shampoo washing, conditioner treatment and drying are repeated and exposure for 15 hours are repeated four more times. Sun damage is determined spectrophotometrically by determining quantity of tryptophan reduction according to method described in C. M. Pande and J. Jachowicz, J. Soc. Cosmet. Chem. 44, 109-122, 1993. Hair switches treated with shampoo and conditioner containing polymer-grafted titanium dioxide particles from Example 1 show less color tryptophan loss (and, therefore, much less photodamage) in exposed area.

The responsive nature of grafted particles from Example 1 allows them to deposit at similar efficiency on hair of various surface energies (oxidative conditions). This results in more effective deposition of the other hydrophobic conditioning actives to the oxidized hair. Usually, these actives would prefer hydrophobic surfaces.

Sunscreens

Example 40

Preparation of Sunscreen

A water based sunscreen is prepared containing the following:

| Ingredient | Wt. % |
|---|---|
| Phase A | |
| Cetyl dimethicon copolyol and polyglycerol-4 isostearate and hexyl laurate (Abil WE-09) | 5.0% |
| Mineral oil | 5.0% |
| Octyl stearate | 6.0% |
| Cyclomethicone | 4.0% |
| Cetyl dimethicone | 1.0% |
| Isopropyl myristate | 4.0% |
| Hydrogenated castor oil | 0.8% |
| Microcrystalline wax | 1.2% |
| Phase B | |
| Water | 62.2% |
| Titanium dioxide P25 (supplied by Degussa) | 10.0% |
| Sodium chloride | 0.8% |

Heat Phase A and stir to dissolve waxes. For phase B, dissolve salt in water, add titanium dioxide to disperse using media milling (dispersion process described in Example 3). Combine phases while homogenizing.

Example 41

Preparation of Sunscreen Containing Grafted Titanium Dioxide Particles from Example 1

Preparation of Example 40 is repeated replacing Phase B with the aqueous dispersion that is prepared in Example 1. Concentration of grafted particles dispersion from Example 1 is adjusted to 10.0% by weight.

A panel study with 10 panelists is performed in order to determine UV protection, skin whitening after sunscreen application, and skin feel on application. Example 40 contains 10% titanium dioxide (13.7% of Phase B). Although sunscreen from Example 41 contains less titanium dioxide by weight than sunscreen from Example A, the SPF values of the sunscreens are the same. In addition, panelists express preference for sunscreen from example 41 as more transparent (appearing less white upon application) as well as having better sensory properties on skin (less heavy and draggy feel).

The expected good performance of sunscreen from Example 41 is a result of two major factors:
  a. Titanium dioxide particles from Example 1 that are used in the sunscreen of Example 41 form stable dispersions in both aqueous and silicone fluids. This is the result of the grafted hydrophilic and hydrophobic polymeric chains that provide steric stabilization in non-polar media (such as silicone fluids) and both steric and electrostatic stabilization in aqueous media. Therefore, aggregation is minimal even if particles migration from one phase of an emulsion to the other occurs. When particles migrate to a different phase severe aggregation is observed, because the surfactants/dispersants molecules that are used to prevent aggregation a usually able to function under specific medium conditions. The problem is more pronounced in cases such as sunscreens where product performance depends on the presence of nanoparticulate materials (very small particle size 50-200 nanometers). In these cases, particle stability is more difficult to achieve and sustain. Lack of stability in terms of aggregation results in particle size increase over time and/or during application and drying on the skin. As a consequence, loss of UV protection efficiency and increased opacity are observed. Increase in opacity means that applied sunscreen liquid appears white both immediately after application and after drying on the skin.

b. The viscosity of dispersions is strongly influenced by the interactions between particles. In the absence of significant surface charges or materials that can adsorb on the surfaces and prevent particles from coming close to each other, attractive forces increase the viscoelasticity of the dispersion. The "heavy" or "draggy" skin feel that consumers describe as a negative feature of sunscreens is the result of inter-particle interactions. Sunscreen of Example 41 shows improved skin feel during application because the grafted polymeric chains prevent significant interparticle interactions.

This concept can also be reapplied to prepare liquid make-up with UV protection, skin care products with UV protection, and hair products with UV protection Further Discussion of Selected Examples Titanium dioxide particles from Example 2 form stable dispersions in both aqueous, lipophilic, and silicone fluids. This is the result of the grafted hydrophilic and hydrophobic polymeric chains that provide steric stabilization in non-polar media (such as silicone fluids) and both steric and electrostatic stabilization in aqueous media.

Examples 6, 9 and 10 show that responsive grafted particles are dispersible/compatible in a variety of media that are used in color cosmetics (silicones, castor oil, water).

Pigment grade titanium dioxide is a typical opacifying material used in color cosmetics. Particles from Example 2 can replace currently used titanium dioxide in a variety of color cosmetics (lipsticks, make up emulsions, etc; see Examples 15, 16, 25, 28, 32). Currently, color cosmetic formulators use specific opacifying and color pigments material for each kind of formulation. Therefore, there is a proliferation of such raw materials. A popular approach to achieve formula compatibility is particle surface modification by reaction or adsorption of oligomers and polymers. Most of the grafted materials used today are poor stabilizers towards aggregation. Responsive grafted particles from Example 2 have the ability to not only compatibilize particles with medium but also stabilize towards aggregation.

This stability towards aggregation is expected to provide benefits in emulsion products such as liquid make ups. When particles migrate from one phase of the emulsion to the other phase, severe aggregation is usually observed, because the surfactants/dispersants molecules that are used to prevent aggregation are usually able to function under specific medium conditions. Therefore, particle stability is more difficult to achieve and sustain in emulsions. Responsive grafted particles will not show similar problems because of the stability they show in various media.

Aggregation may also happen during drying of the film. Grafted material contain long polymeric chains of different polarity that keep the particles separated even when polarity of the medium change dramatically due to evaporation.

A typical consumer complaint is also related to pore and wrinkle more pronounced appearance after the application of liquid make up. This is also related to particle aggregation and settling of large particles on crevices of skin. This can also be prevented by particle stabilization via polymeric chains.

Lack of aggregation stability results in pigment particle size increase. As titanium dioxide particles aggregate from approximately 0.5 micrometers to multi-micrometers, transparency of the film increases. Decrease in opacity is translated to consumer perception of lower skin coverage. Dark spots and skin imperfections are more apparent and product is perceived as poor performing.

Shade shift from wet to dry film is also related to titanium dioxide aggregation. As mentioned above, as titanium dioxide particles aggregate, their opacifying and color diluting characteristics decrease. Therefore, color appears stronger and film appears darker because the effects of the other colored pigments are more pronounced (less white).

Grafted titanium dioxide of the present invention is also easier to be removed from skin using soap/water or aqueous wipes (especially if pH is acidic). The responsive nature of these particles contributes to switching of their surface to hydrophilic when the medium becomes hydrophilic. Therefore, particles will respond to the aqueous environment of the wipe by coiling of the PDMS chains (that were extended on dry film) and extending of the hydrophilic chains (that were coiled on dry film). This results in increased hydrophilicity of the make up film and better removability with aqueous cleaning systems (soap/water or wipes). Example 28 is related to this concept.

The fact that the responsive grafted particles are stable toward aggregation in various media without the need for other formulation additives, makes formulation development process easy.

When micronized grafted particles related to the present invention are used in film-forming cosmetic products, the high surface area of the particles (small particle size) may provide film strengthening (stronger film, less flaking; see mascara Example 32). In cases with multi-layer films of various polarities, stronger adhesion may be expected.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited are incorporated herein by reference in their entirety; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal care composition comprising:
   (a) a responsive particle, wherein said responsive particle comprises:
      (1) a particle core having an interfacial surface; wherein said particle core is an inorganic particle core selected from the group consisting of titanium dioxide, silica, iron oxides, zinc oxide, micas, zeolites, boron nitride, talc and mixtures thereof;
      (2) a first polymer, wherein said first polymer is polyethylenimine; and
      (3) a second polymer, wherein said second polymer is aminopropyl-terminated polydimethylsiloxane
   wherein said first polymer and said second polymer are covalently attached to the interfacial surface of said particle core at different locations on said interfacial surface; wherein the properties of the responsive particle change in response to changes in the environment; and wherein the properties of the responsive particle are selected from the group consisting of surface energy, hydrophilicity, hydrophobicity, acidity, basicity, and charge; and
   (b) a dermatologically acceptable carrier.

2. The personal care composition of claim 1, wherein said personal care composition is selected from the group consisting of lipstick, mascara, rouge, foundation, blush, eyeliner, lipliner, lip gloss, facial powder, body powder, sunscreen, sun block, nail polish, mousse, spray, styling gel, nail conditioner, bath gel, shower gel, shampoo, conditioner, cream rinse, hair dye, hair coloring product, hair conditioner, lip balm, skin conditioner, cold cream, moisturizer, hair spray, soap, body scrub, exfoliant, astringent, depilatory, permanent waving solution, antidandruff formulation, antiperspirant composition, deodorant, shaving product, preshaving product, after shaving product, cleanser, skin gel, and rinse.

3. A method for making a responsive particle for use in personal care compositions, comprising:
   (1) providing a particle core having an interfacial surface; wherein said particle core is an inorganic particle core selected from the group consisting of titanium dioxide, silica, iron oxides, zinc oxide, micas, zeolites, boron nitride, talc and mixtures thereof
   (2) attaching a first polymer having a first property to said interfacial surface; and
   (3) attaching a second polymer having a contrasting property to said interfacial surface
   wherein the first polymer is polyethylenimine, and wherein said second polymer is aminopropyl-terminated polydimethylsiloxane.

4. The method of claim 3, wherein said personal care composition is selected from the group consisting of lipstick, mascara, rouge, foundation, blush, eyeliner, lipliner, lip gloss, facial powder, body powder, sunscreen, sun block, nail polish, mousse, spray, styling gel, nail conditioner, bath gel, shower gel, shampoo, conditioner, cream rinse, hair dye, hair coloring product, hair conditioner, lip balm, skin conditioner, cold cream, moisturizer, hair spray, soap, body scrub, exfoliant, astringent, depilatory, permanent waving solution, antidandruff formulation, antiperspirant composition, deodorant, shaving product, preshaving product, after shaving product, cleanser, skin gel, and rinse.

5. The personal care composition of claim 1, wherein said particle core is selected from the group consisting of zinc oxide, titanium dioxide, and mixtures there.

6. A personal care composition comprising:
   (a) a responsive particle, wherein said responsive particle comprises:
      (1) a particle core having an interfacial surface; wherein said particle core is an inorganic particle core selected from the group consisting of titanium dioxide, zinc oxide, and mixtures thereof;
      (2) a first polymer having a first property; wherein said first polymer is polyethylenimine
      (3) a second polymer having a contrasting property; wherein said second polymer is aminopropyl-terminated polydimethylsiloxane
   wherein said first polymer and said second polymer are covalently attached to the interfacial surface of said particle core at different locations on said interfacial surface; wherein the properties of the responsive particle change in response to changes in the environment; and wherein the properties of the responsive particle are selected from the group consisting of surface energy, hydrophilicity, hydrophobicity, acidity, basicity, and charge; and
   (b) a dermatologically acceptable carrier.

* * * * *